(12) United States Patent
Park et al.

(10) Patent No.: US 6,904,320 B2
(45) Date of Patent: Jun. 7, 2005

(54) SLEEP APNEA THERAPY DEVICE USING DYNAMIC OVERDRIVE PACING

(75) Inventors: Euljoon Park, Stevenson Ranch, CA (US); Gene A. Bornzin, Simi Valley, CA (US); Paul A. Levine, Santa Clarita, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/077,053

(22) Filed: Feb. 14, 2002

(65) Prior Publication Data

US 2003/0153954 A1 Aug. 14, 2003

(51) Int. Cl.$^7$ ................................................ A61N 1/18
(52) U.S. Cl. ........................................................ 607/17
(58) Field of Search ...................................... 607/4–28

(56) References Cited

U.S. PATENT DOCUMENTS

| | | |
|---|---|---|
| 4,644,954 A | 2/1987 | Wittkampf et al. ... 128/419 PG |
| 4,759,366 A | 7/1988 | Callaghan ............. 128/419 PG |
| 4,815,469 A | 3/1989 | Cohen et al. ................ 128/634 |
| 5,040,538 A | 8/1991 | Mortazavi .................... 128/633 |
| 5,113,869 A | 5/1992 | Nappholz et al. ........... 128/696 |
| 5,161,527 A | 11/1992 | Nappholz et al. ..... 128/419 PG |
| 5,184,615 A | 2/1993 | Nappholz et al. ..... 128/419 PG |
| 5,188,106 A | 2/1993 | Nappholz et al. ..... 128/419 PG |
| 5,466,254 A | 11/1995 | Helland ....................... 607/123 |
| 5,476,483 A | 12/1995 | Bornzin et al. ................ 607/17 |
| 5,485,851 A | 1/1996 | Erickson ...................... 128/716 |
| 5,549,650 A | 8/1996 | Bornzin et al. ................ 607/24 |
| 5,614,246 A | 3/1997 | Mund et al. ................ 427/2.24 |
| 5,626,622 A | 5/1997 | Cooper ......................... 607/18 |
| 5,643,327 A | 7/1997 | Dawson et al. ............... 607/24 |
| 5,778,223 A | 7/1998 | Velissaropoulos et al. .. 395/611 |
| 5,800,467 A | 9/1998 | Park et al. ..................... 607/17 |

(Continued)

FOREIGN PATENT DOCUMENTS

| | | | |
|---|---|---|---|
| EP | 0 940 155 A2 | 2/1999 | ............ A61N/1/36 |
| EP | 1 151 718 A2 | 4/2001 | ......... A61B/5/0205 |
| EP | 1 295 623 A1 | 9/2002 | ............ A61N/1/37 |
| WO | WO 00/01438 | 1/2000 | ......... A61M/16/00 |

OTHER PUBLICATIONS

Millar, et al., "The Entrainment of Low Frequency Breathing Periodicity", CHEST/98/5, pp:1143–1148 (Nov. 1990).

Hanly, et al., "Respiration and Abnormal Sleep in Patients with Congestive Heart Failure", CHEST/96/3, pp: 480–488 (Sep. 1989).

Saul, et al., "Nonlinear Interactions Between Respiration and Heart Rate: Classical Physiology or Entrained Nonlinear Oscillators", IEEE, pp: 299–300 (1989).

Garrigue, et al., "Night Atrial Overdrive with DDD Pacing Results in a Significant Reduction of Sleep Apnea Episodes and QOL Improvement in Heart Failure Patients", NASPE (2001).

Balaban, et al., "Feasibility of Screening for Sleep Apnea Using Pacemaker Impedance Sensor", PACE, vol. 24, Part II, No. 313, pp: 617 (Apr. 2001).

Bornzin, et al., "Adjusting Heart Rate During Sleep Using Activity Variance", PACE, vol. 17, Part II, pp: 1933–1938 (Nov. 1994).

(Continued)

*Primary Examiner*—Scott M. Getzow

(57) ABSTRACT

A cardiac stimulation device uses dynamic overdrive pacing to prevent sleep apnea. In another aspect, the device can use dynamic overdrive pacing to terminate sleep apnea after detection. An implantable cardiac stimulation device comprises a sensor and one or more pulse generators. The sensor senses intrinsic cardiac electrical phenomena. The pulse generators can generate cardiac pacing pulses with timing based on the sensed intrinsic cardiac electrical phenomena to dynamically overdrive the intrinsic cardiac electrical phenomena. The timed cardiac pacing pulses can prevent a sleep apnea condition.

29 Claims, 7 Drawing Sheets

U.S. PATENT DOCUMENTS

| | | | |
|---|---|---|---|
| 5,819,062 A | 10/1998 | Srikantappa | 395/500 |
| 5,970,494 A | 10/1999 | Velissaropoulos et al. | 707/102 |
| 5,974,340 A | 10/1999 | Kadhiresan | 607/18 |
| 5,991,661 A | 11/1999 | Park et al. | 607/19 |
| 6,029,088 A | 2/2000 | Budgifvars et al. | 607/27 |
| 6,052,622 A | 4/2000 | Holmström | 607/28 |
| 6,058,328 A | 5/2000 | Levine et al. | 607/14 |
| 6,064,910 A | 5/2000 | Andersson et al. | 607/20 |
| 6,126,611 A | 10/2000 | Bourgeois et al. | 600/529 |
| 6,128,534 A | 10/2000 | Park et al. | 607/17 |
| 6,132,384 A | 10/2000 | Christopherson et al. | 600/529 |
| 6,259,948 B1 | 7/2001 | Florio et al. | 607/9 |
| 6,266,564 B1 | 7/2001 | Hill et al. | 607/9 |
| 6,272,381 B1 | 8/2001 | Callaghan et al. | 607/26 |
| 6,480,733 B1 | 11/2002 | Turcott | 600/516 |
| 6,574,507 B1 | 6/2003 | Bonnet | 607/20 |
| 2002/0193697 A1 | 12/2002 | Cho et al. | 600/529 |

OTHER PUBLICATIONS

Stephane Garrigue, M.D., et al. "Benefit of Atrial Pacing in Sleep Apnea Syndrome," *New England Journal of Med.*, 2002; vol. 346, No. 6(2), pp. 404–412.

Krzysztof W. Balaban, M.D., et al. "O2 Saturation During Sleep Correlates Significantly With Pacing Lower Rate in Patients With Sleep Apnea," *PACE 2002*; vol. 24, 25 (Park II): p. 658, No. Abstract No. 544.

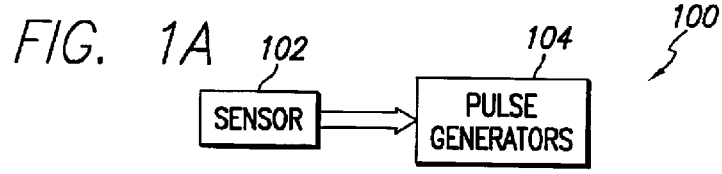
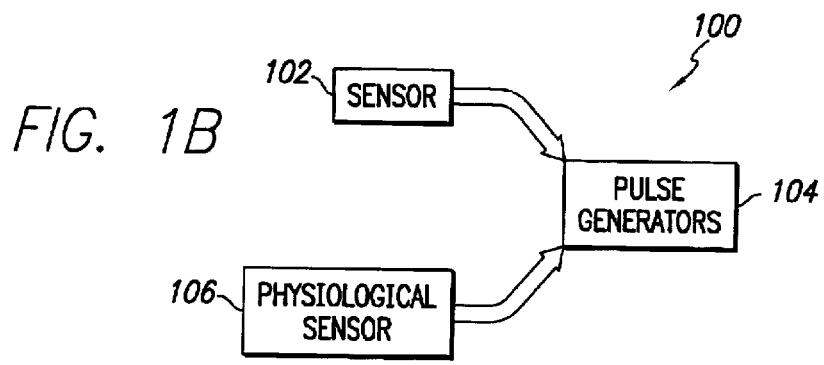
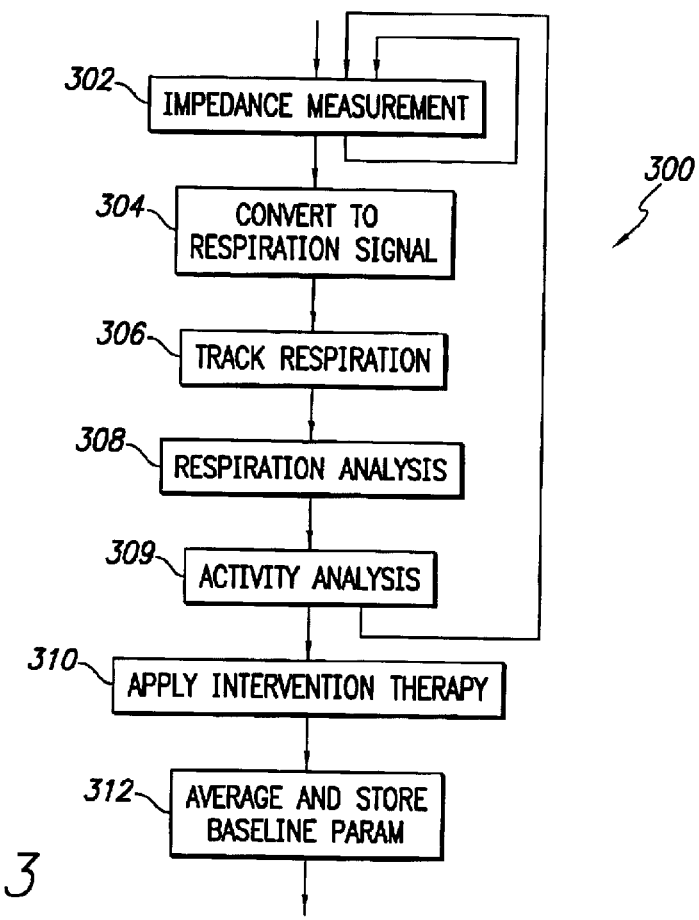
FIG. 3

SLEEP APNEA THERAPY DEVICE USING DYNAMIC OVERDRIVE PACING

CROSS-REFERENCE TO RELATED APPLICATIONS

This application is related to copending, commonly-assigned U.S. patent application Ser. No. 10/077,660, titled CARDIAC STIMULATION DEVICE INCLUDING SLEEP APNEA PREVENTION AND TREATMENT; and U.S. patent application Ser. No. 10/077,048, titled STIMULATION DEVICE FOR SLEEP APNEA PREVENTION, DETECTION AND TREATMENT; both applications filed Feb. 14, 2002.

FIELD OF THE INVENTION

The present invention relates to techniques for providing therapy to patients who suffer from sleep apnea.

BACKGROUND OF THE INVENTION

Sleep apnea is the cessation of breathing for a short time while sleeping. Sleep apnea has multiple classifications based on source of dysfunction. Obstructive sleep apnea results from mechanical blockage of the airway, for example due to weight of fatty neck tissue compressing the trachea. Central sleep apnea results from neurological dysfunction. Mixed sleep apnea has a combination of mechanical and neurological cause.

Upper airways of the nose and pharynx are held open during breathing by dilator muscles that counteract pressure gradients that would otherwise cause airway collapse. In obstructive sleep apnea, mechanical airway obstruction resulting from superior airway size reduction, increase in airway compliance, and reduction in airway muscle tone leads to pressure disequilibrium that tends to collapse the airways.

The nervous system controls activity of the dilator muscles and respiratory muscles, resulting in a coordinated response to stimulation or depression. Ventilatory fluctuations of hyperventilation and hypoventilation occur during sleep to facilitate breathing without conscious control, reducing the work required for breathing. Unfortunately, in obstructive sleep apnea the ventilatory fluctuations allow superior airway instability and oropharyngeal obstruction, exacerbating the difficulties and dangers of sleep apnea.

Similarly, nervous system interactions of respiratory and cardiovascular functions tend to worsen the problems that arise in sleep apnea. Cardiac arrhythmia conditions such as bradycardia, tachyarrhythmia, atrioventricular block, and ventricular extrasystole are aggravated by obstructive sleep apnea, stimulating the autonomic nervous system and further degrading respiratory performance.

Central sleep apnea is cessation of breathing due to neurological dysfunction, for example a failure to generate neuro-muscular stimulation required to initiate and control a respiratory cycle. The neurological dysfunction are believed to originate in the Thalmus area of the brain and may involve primary brainstem medullary depression resulting from a tumor of the posterior fossa, poliomyletis, or idiopathic central hypoventilation. During a central sleep apnea episode, a patient may fail to breath for an extended time, for example a few seconds up to two or more minutes, then rapidly inhale, typically upon arousal from sleep.

FIG. 8 is a graph that illustrates the mechanism of sleep apnea by correlating ventilatory effort to arterial partial pressure of carbon dioxide ($PaCO_2$). Ventilatory effort is generally greater during waking conditions than while asleep. Onset of sleep results in two phenomena. First, the onset of sleep causes an increased threshold 810 for blood carbon dioxide concentration. Second, gain or slope ($\Delta V/\Delta PaCO_2$) of the ventilatory effort increases. The increase in $PaCO_2$ threshold during sleep allows one to breathe a smaller volume of air. During sleep apnea, collapse of ventilation airways causes a decrease in arterial oxygen concentration ($PaO_2$). Arousal from sleep caused by body defense mechanisms increases upper airway muscle tone, causing the airway to open and arterial oxygen concentration to increase, thereby satisfying body oxygen requirements but setting the stage for a subsequent apnea episode.

Symptoms of sleep apnea include snoring, breath holding during sleep, rapid awakening with gasping for air, morning headaches, depression, irritability, loss of memory, lack of energy, high risk of automobile and workplace accidents, and lack of high quality sleep and resulting daytime grogginess and sleepiness.

Sleep apnea is rarely fatal but is linked to high blood pressure and increased probability of heart disease, stroke, and arrhythmias. Patients with coronary artery disease who have a blood oxygen level lowered by sleep-disordered breathing may be at risk of ventricular arrhythmia and nocturnal sudden death. Furthermore, sleep-disordered breathing may cause coronary artery disease and hypertension.

Various treatments exist for sleep apnea including medical device treatments, surgery, and drugs. The type of treatment depends on the type of sleep apnea and, for obstructive apnea, the type and location of airway obstruction and the patient's health condition. Obstructions can occur in the nose or pharynx. Obstructions in the nose may result from a deviated septum or swollen nasal passages. Obstructions in the upper pharynx may result from enlarged adenoids, long soft palate, large uvula, or large tonsils. Obstructions in the lower pharynx may result from a large or posterior-placed tongue, short jaw, or short and wide neck. Drug therapy is usually sufficient for sleep apnea treatment.

Device treatments may be separated into air pressure devices and neural stimulation devices.

The most common pressure device treatment is termed continuous positive airway pressure (CPAP) and utilizes a mask worn over the nose while sleeping. A hose connects the mask to an air pump that supplies a constant controlled air pressure to a patient's nasal passages and the trachea, preventing collapse. CPAP supplies a continuous, stable pre-determined volume of air to the nasal mask to prevent the airway passage from collapsing.

Bi-level positive airway pressure (BiPAP) treatment is related and similar to CPAP except that BiPAP allows for a reduction in airflow pressure that occurs during expiration. BiPAP allows setting of two different airway pressure levels to avoid fighting incoming air pressure in the expiration portion of the respiratory cycle.

Effectiveness of CPAP varies greatly. Some believe that CPAP is an effective treatment for sleep apnea, but is inconvenient and bothersome to use. Others believe CPAP offers little help in sleep apnea treatment. Still others relate that CPAP is harmful and actually causes sleep apnea episodes since the lung is forced into a constant elevated positive pressure. Normally the lung pressure oscillates between a negative and positive pressure.

Another problem with CPAP and BiPAP devices is the inherent inconvenience and burden of wearing a constricting mask for the sleeping hours, resulting in poor patient compliance with a treatment program.

Various neural stimulation devices are known that generate and apply electrical signals that stimulate nerves to recruit upper airway muscles and maintain muscle tone in the upper airways. Several types of sensing have been used to determine appropriate timing for delivery of muscle stimulation including monitoring of inspiratory effort, respiratory functioning, breathing through the nostrils, and electrical activity associated with contractions of the diaphragm. Problems with neural stimulation include the difficulty of ensuring stimulation of correct muscular structures in the upper airways of a particular patient since the hypoglossal nerve is nearby other structures which should not be stimulated with the structures located differently in different patients.

In addition to device treatments for sleep apnea, various surgical treatments are available. Uvulopalatopharyngoplasty (UPPP) surgery removes fleshy tissue of the uvula and tightens soft tissue of the palate and pharynx in an effort to reduce or remove tissue responsible for obstruction. Unfortunately, UPPP involves significant surgical risks including airway swelling, bleeding, considerable pain for days or weeks, and depression of breathing reflex due to application of general anesthetic, a substantial problem for sleep apnea patients with difficulty breathing while not under anesthesia. Furthermore, effectiveness rates for UPPP are low, on the order of 50% effectiveness in about 50% of patients undergoing the operation.

Laser-assisted uvulaplasty (LUAP) is a laser surgery on the uvula and soft palate that is reported to reduce snoring, but having no controlled studies that show effectiveness in reducing sleep apnea. A major problem with LUAP is that snoring is known not merely as a symptom of sleep apnea, but also as a warning sign of a sleep apnea episode. By silencing the warning provided by snoring, a patient may continue with untreated sleep apnea which may worsen but be ignored.

Pharmaceuticals and medicines are also known treatments for sleep apnea. For example, anti-depressants such as protriptyline or depressants such as klonopin are sometimes prescribed for sleep apnea but appear to be marginally effective.

SUMMARY OF THE INVENTION

In accordance with one aspect of the present invention, a cardiac stimulation device uses dynamic overdrive pacing to prevent sleep apnea. In another aspect, the device can use dynamic overdrive pacing to terminate sleep apnea after detection.

In accordance with an embodiment of the present invention, an implantable cardiac stimulation device comprises a sensor and one or more pulse generators. The sensor senses intrinsic cardiac electrical phenomena. The pulse generators can generate cardiac pacing pulses with timing based on the sensed intrinsic cardiac electrical phenomena to dynamically overdrive the intrinsic cardiac electrical phenomena. The timed cardiac pacing pulses can prevent a sleep apnea condition.

In another embodiment, a cardiac stimulation device comprises a sensor and one or more pulse generators. The sensor senses intrinsic cardiac electrical phenomena. The pulse generators can generate cardiac pacing pulses with timing based on the sensed intrinsic cardiac electrical phenomena to dynamically overdrive the intrinsic cardiac electrical phenomena. The timed cardiac pacing pulses can terminate a sleep apnea condition.

In one aspect of the invention, a method of operating an implantable cardiac stimulation device comprises monitoring cardiac electrical signals, sensing intrinsic cardiac electrical phenomena based on the monitored signals, and generating cardiac pacing pulses with a dynamic overdrive timing based on the intrinsic cardiac electrical phenomena. The dynamic overdrive pacing prevents a sleep apnea for a sleeping patient, and, terminates the sleep apnea condition upon occurrence.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

FIGS. 1A and 1B are highly schematic block diagrams that depict examples of implantable cardiac stimulation devices capable of preventing and treating sleep apnea using dynamic overdrive pacing.

FIG. 3 is a flow chart that depicts an example of a technique for detecting Cheyne-Stokes respiration by monitoring respiration signals and treating the condition using dynamic overdrive pacing.

DESCRIPTION OF THE EMBODIMENT(S)

Figure 2:
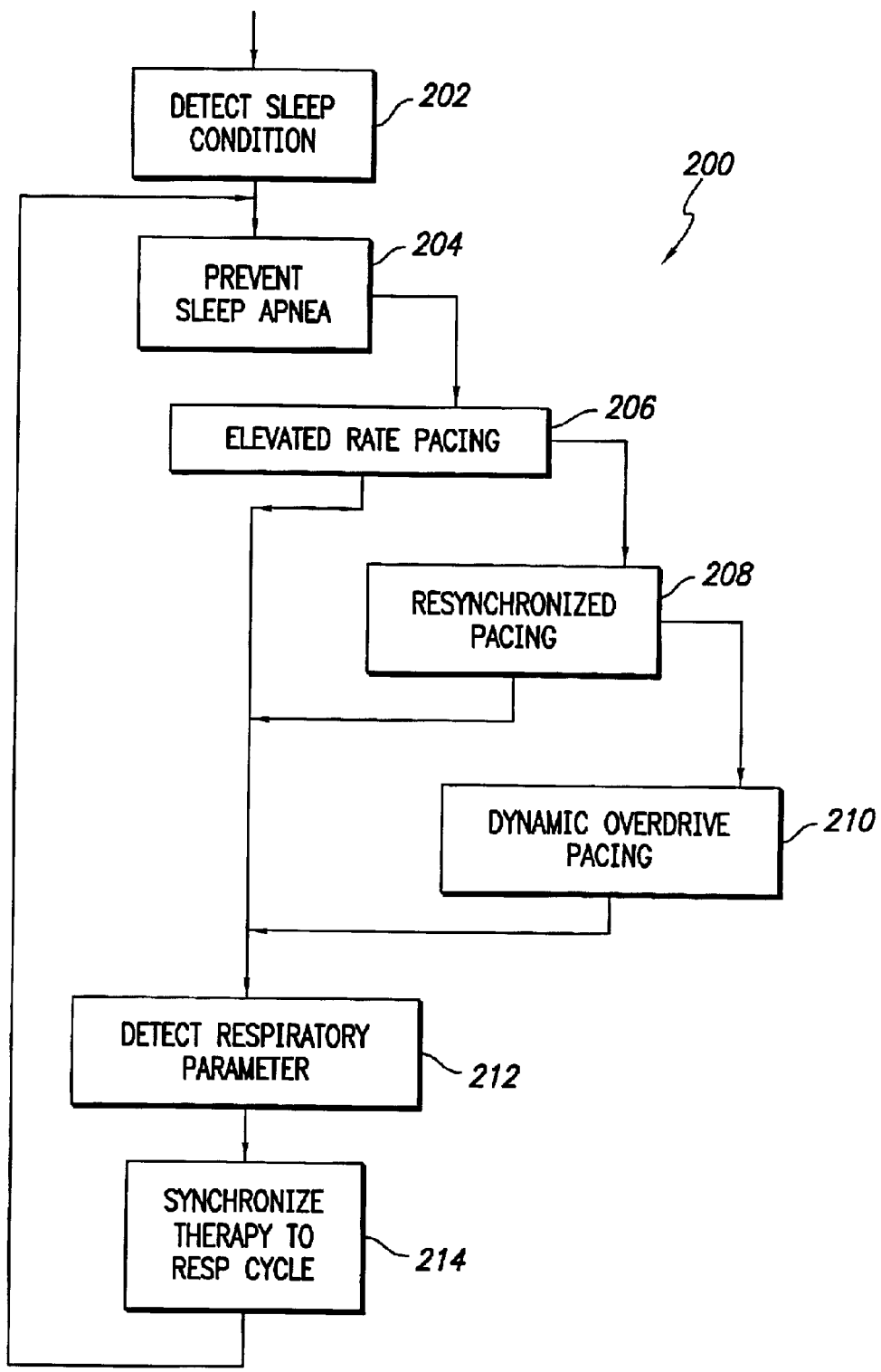
FIG. 2 is a schematic flow chart that illustrates actions of an implantable stimulation device that prevents and treats sleep apnea using dynamic overdrive pacing.

The following describes the best mode presently contemplated for practicing the invention. The description is not to be taken in a limiting sense but is set forth to convey the general principles of operation and structure of the illustrative embodiments. The issued claims define the invention scope. In the following description, like numerals or reference designators refer to like parts or elements throughout.

Referring to FIG. 1A, a highly schematic block diagram depicts an example of an implantable cardiac stimulation device 100 that includes a sensor 102 and one or more pulse generators 104. The sensor 102 is capable of sensing intrinsic cardiac electrical phenomena. The pulse generators 104 are configured to generate cardiac pacing pulses with timing based on the sensed intrinsic cardiac electrical phenomena to dynamically overdrive the intrinsic cardiac electrical phenomena. The pulse generators 104 increase pacing rate during the sleeping state to prevent sleep apnea. The timed cardiac pacing pulses generally prevent a sleep apnea condition by pacing at a rate that is greater than the patient's intrinsic rate while sleeping. The elevated pacing rate tends to prevent the occurrence of sleep apnea. The timed cardiac pacing pulses can also terminate a sleep apnea condition.

In a more specific example, a cardiac stimulation device 100 can be configured to pace a patient's heart according to a rest mode of operation. In the rest mode, the physiological sensor 102 may be used to determine a suitable heart rate based on the patient's intrinsic heart rate, such as the patient's intrinsic rate of atrial depolarizations. When the patient is awake but not undergoing physical or psychological stress, the cardiac rate is set to a suitable average rate for the resting level of activity. The resting rate is typically set according to various calibrated parameters that can be programmed by a health care worker or can be automatically determined. When the patient sleeps, the metabolic demand is reduced so that the heart rate may also be reduced. The cardiac stimulation device 100 may detect the sleep condition based on cardiac depolarization signals or signals from other types of sensors. These sensors may be termed "physiological sensors" even though the sensed parameter may not strictly relate to a physiology. For example, the signals may be indicative of activity or activity variance, respiration, minute ventilation, cardiac conductivity, blood oxygen concentration, stroke volume, and others. Still other suitable parameters include parameters based on sensing of cardiac electrical signals, the parameters including QT interval, evoked response integral, stroke volume, paced depolarization integral (PDI), and others.

Various sensors are known to those having ordinary skill in the art that may be used to measure blood oxygen and/or blood carbon dioxide concentration. Fiber optic $PCO_2$ sensors and $PO_2$ sensors are known that are suitable for blood concentration measurements. One example is a combined Clark-type PO2/Stow-Severinghaus type PCO2 sensor for sensing both $PaO_2$ and $PaCO_2$. Other sensors include gel polymeric electrodes that contain a suitable electrolyte for measuring a selected parameter such as $PCO_2$, $PO_2$, or pH. Various other sensors may be suitable including optical fiber pH sensors, optical fiber $PCO_2$ sensors, thermocouple temperature sensors. Suitable $PO_2$ sensors may be electrochemical $PO_2$ sensors or a fluorescent $PO_2$ sensors.

In an alternative example, sleeping hours may be simply selected by the patient or health care provider using telemetric programming.

In a device that is configured to prevent, detect, and terminate sleep apnea, the sleeping rate is set higher than the resting rate to prevent sleep apnea. The particular rate to prevent sleep apnea may be set using dynamic overdrive pacing. In one embodiment, the cardiac stimulation device 100 may activate dynamic overdrive pacing once the patient begins sleeping. In dynamic overdrive pacing, the cardiac stimulation device 100 senses intrinsic cardiac depolarizations using the sensor 102. The cardiac stimulation device 100 controls the rate or timing of pacing pulses by the pulse generators 104 to predominantly pace the heart in most cardiac cycles and reduce or minimize the number of cardiac cycles in which intrinsic pulses inhibit pulse generation.

Referring to FIG. 1B, some embodiments may include a physiological sensor 106 that senses physical motion or metabolic demand and can be used to detect either a sleeping state or a sleep apnea condition. In one example, an impedance sensor may be used to detect respiration parameters including, for example, respiration rate and minute volume.

In addition to preventing sleep apnea, the cardiac stimulation device 100 may detect respiratory difficulties such as episodes of sleep apnea using the physiological sensor 102 and invoke dynamic overdrive pacing to treat sleep apnea. A system that includes an impedance sensor for sensing respiratory parameters can track respiration to integrate overdrive pacing with periodic breathing.

In another embodiment, the cardiac stimulation device 100 may prevent sleep apnea using a tiered therapy including an elevated pacing rate stage, a resynchronization stage, and a dynamic overdrive stage. In the elevated pacing stage, the pacing rate is raised to a preset level or to a level that is a preselected increment over the average rate obtained by monitoring over an extended time. In the resynchronization stage, the pacing rate is slowly reduced to resynchronize with the patient's intrinsic rate or to a preset base rate. In the dynamic overdrive stage, the pacing rate is increased over the intrinsic rate to assure that the pacing rate is at least slightly faster than the intrinsic rate.

Referring to FIG. 2, a schematic flow chart illustrates actions of the implantable cardiac stimulation device 100 with a sensor 102 and one or more pulse generators 104 and a capability to prevent or treat sleep apnea using dynamic overdrive pacing. The flow chart describes an overview of the operation and features implemented in one embodiment of the device. In the flow chart, and the additional flow charts described herein, the various acts are summarized in individual actions. The actions or decisions are performed as the operation proceeds. Where a processor or equivalent element is employed, flow charts may describe operations of a control program or executable control logic that may be used by such a processor or equivalent element to effectuate desired control of the stimulation device. Those having ordinary skill in the art can readily write such a control program based on the flow charts and other descriptions presented herein.

The cardiac stimulation device 100 is responsive to a signal that indicates a patient's sleeping condition in a detect sleep condition action 202. Various techniques may be used to detect the sleep condition such as sensing of a reduced metabolic demand or physical activity using various physiological or motion sensors, sensing of a reduced heart rate by a cardiac electrical signal sensor. In simple examples, the sleep condition may be activated simply by a signal from a real-time clock indicative of when the patient intends to sleep.

Upon detection of the sleep condition, the cardiac stimulation device 100, begins a therapy for prevention of sleep apnea 204. In one example, the therapy is dynamic overdrive pacing 210. In another example, the therapy is pacing at an elevated rate 206. In a further example, a tiered therapy includes pacing at the intrinsic atrial rate, followed by resynchronized pacing 208. In another example of a tiered therapy, either elevated rate pacing 206 or dynamic overdrive pacing 210 is applied as a first tier, followed by resynchronized pacing 208. In another example, a tiered therapy is executed including pacing at a high rate 206, resynchronizing 208, and dynamic overdrive pacing 210. In the high pacing rate action 206, the cardiac stimulation device typically elevates the pacing rate to a level that is assured to pace the heart. For example, a patient with an intrinsic rate of 65 bpm may be paced at 80 bpm during the high pacing rate action 206. Alternatively, the cardiac stimulation device, upon first detecting a patient's sleeping state, may increase the pacing rate to a preset level or to a level that is a preselected increment over the average rate obtained by monitoring over an extended time.

The high pacing rate action 206 may last for a selected duration, for example a specified number of cardiac cycles or units of time.

In the tiered therapy, resynchronization 208 is executed by gradually reducing the pacing rate by a selected delta rate or interval until the heart beats at an intrinsic rate or a selected base rate. Following determination of the base rate or intrinsic rate, the tiered therapy activates dynamic overdrive pacing 210.

In systems that include a physiological sensor, dynamic overdrive pacing 210 may be supplemented by detection of respiratory parameters 212 and synchronizing modification of pacing parameters with the respiratory cycle 214. Analysis of the respiration signal may be used to diagnose respiratory disorders. For example, a normal respiratory effort waveform has repetitive inspiratory peaks that are approximately the same amplitude. In contrast, on the onset of apnea, the inspiratory peaks rapidly decrease in amplitude due to increased inspiratory effort in response to difficulty in breathing through the obstructed airway. Accordingly, the overdrive pacing rate may be raised or lowered according to periodic breathing patterns. In one example, the overdrive rate may be reduced during the inspiration stage of breathing.

The cardiac stimulation device controls pacing pulse generation depending on the patient's state, such as sleep, waking, rest, exercise, onset of sleep apnea, and sleep apnea . In one example, for prevention and treatment of sleep apnea the device increases the base rate while sleeping. In one specific example, the stimulation device may increase the resting rate to the base rate. For the onset of sleep apnea, the stimulation device may increase the pacing rate a further amount. Upon detection of a current sleep apnea condition, the device increases the pacing rate even further.

Referring to FIG. 3, a flow chart depicts an example of a technique for detecting Cheyne-Stokes respiration by monitoring respiration signals and treating the condition using dynamic overdrive pacing. Cheyne-Stokes respiration is an abnormal breathing pattern that commonly occurs in patients with decompensated congestive heart failure and neurological diseases. Cardiopulmonary system difficulties associated with Cheyne-Stokes respiration include oxygen desaturation, cardiac arrhythmias, and mental degradation. Cheyne-Stokes respiration appears with periods of tachypnea and hypernea alternating with apnea.

In some embodiments, the stimulation device monitors transthoracic impedance to detect Cheyne-Stokes respiration as a type of sleep apnea, particularly in conditions of congestive heart failure. The stimulation device monitors respiration patterns and parameters that may be indicative of Cheyne-Stokes respiration. Generally, a positive indication of Cheyne-Stokes respiration is shallow breathing or absence of breathing, followed by hypernea with a high respiration rate.

Exercise or physical activity produce respiratory phenomena that are similar to Cheyne-Stokes respiration. In some systems, the stimulation device may include an activity sensor such as an accelerometer or piezoelectric crystal to distinguish Cheyne-Stokes respiration. If a respiratory rate and amplitude increase occurs in association with an increase in activity, then the condition may be classified as activity-related rather than Cheyne-Stokes respiration.

An impedance measurement action 302 periodically measures impedance in the thoracic region of the patient's body, processes the impedance signal, and stores the processed signal. Processing of the impedance signal may include various actions such as amplitude modulation, filtering, other operations that are well known by those having ordinary skill in the art, or may include no operations. Generally, the impedance measurement action 302 repeats in a loop over time to acquire and store a time history of respiration characteristics. A convert to respiration signal action 304 converts the impedance signal to a representation of respiration and typically includes actions such as filtering, time averaging, integration, and the like to determine one or more respiration parameters such as respiration rate, tidal volume, and minute volume.

A respiration tracking action 306 compares the recent respiration signal characteristics with baseline respiration characteristics to determine whether Cheyne-Stokes respiration may be occurring. For example, the current rate may be compared with a long-term average respiration rate. If the current respiration signals are indicative of potential Cheyne-Stokes respiration, then a detailed respiration analysis action 308 includes a more detailed analysis of respiration characteristics. For example, the respiration tracking action 306 may determine whether the current tidal volume exceeds the long-term baseline average tidal volume by a preset threshold percentage. If so, the detailed respiration analysis action 308 monitors and stores respiration parameters for multiple cycles to determine a respiration pattern. For example, tidal volume, respiration rate and minute volume for a plurality of time samples can be acquired and stored to detect characteristics of Cheyne-Stokes respiration. Common Cheyne-Stokes characteristics include abnormally deep and rapid breaths are taken for a few respiratory cycles, followed by shallow and infrequent breathing manifest as low rate and low amplitude respiration. Other Cheyne-Stokes criteria may vary for particular patients. Particular criteria can be established and stored in the stimulation device, typically by a health care provider using the external programmer, although possibly at manufacture. Analysis of impedance and respiration signals can be supplemented with other physiological signals and indicators to improve accuracy, efficiency, or other considerations.

Activity analysis action 309 determines whether exercise or physical activity is the cause of respiratory phenomena that are similar to Cheyne-Stokes respiration. An activity sensor such as an accelerometer or piezoelectric crystal may be used to distinguish Cheyne-Stokes respiration. If a respiratory rate and amplitude increase is coincident with increased activity, the condition may be classified as activity-related rather than Cheyne-Stokes respiration.

If the detailed respiration analysis action 308 and activity analysis action 309 determine the occurrence of Cheyne-Stokes respiration, the stimulation device may initiate an intervention action 310 for a predetermined duration or until Cheyne-Stokes respiration ceases.

In addition to analysis 308 and possible intervention 310, the stimulation device includes long-term averaging and storage of baseline parameters 312.

In one example, intervention 310 treats the sleep apnea condition by dynamic overdrive pacing.

Figure 4:
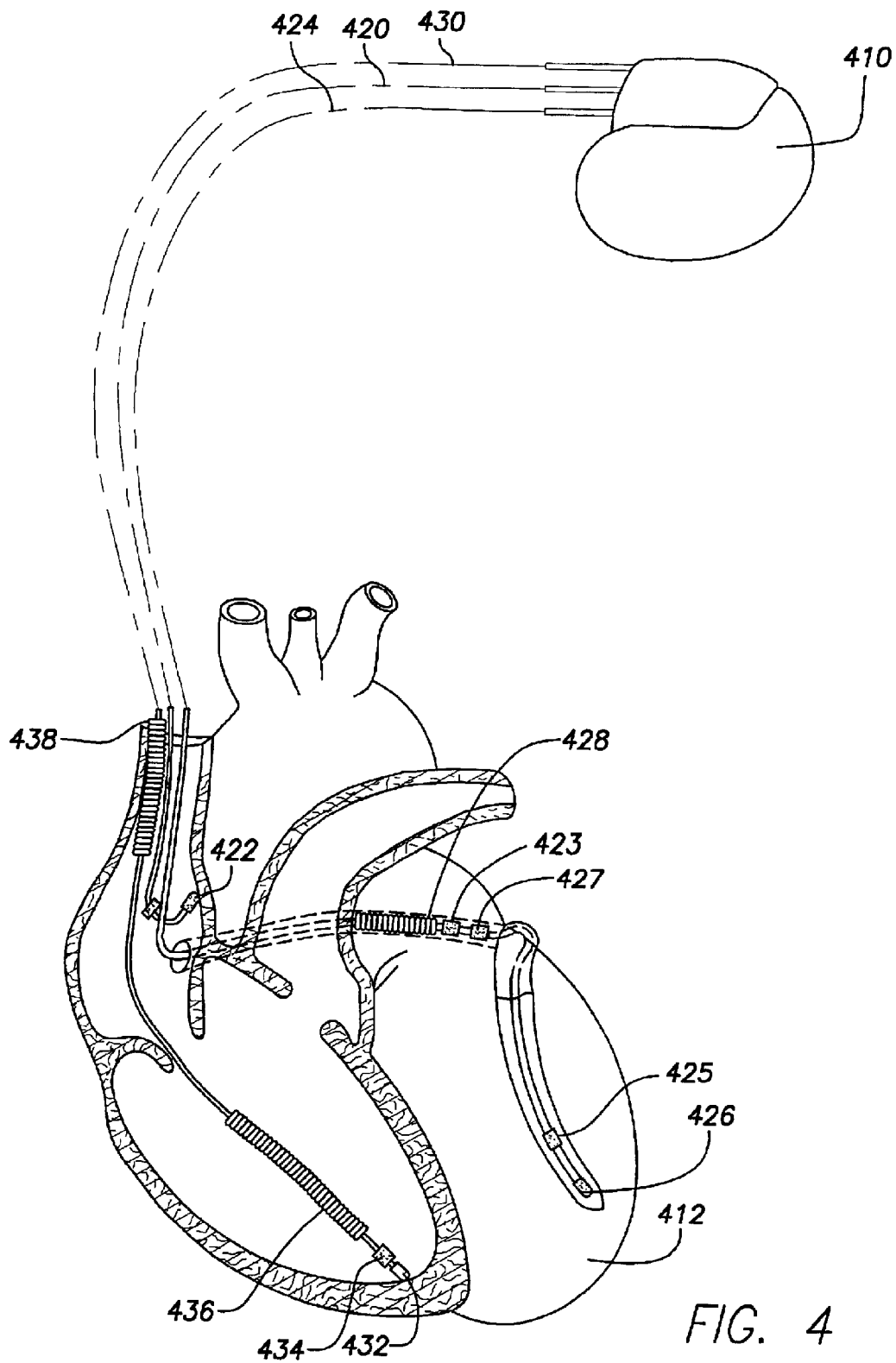
FIG. 4 is a simplified diagram illustrating an implantable stimulation device in electrical communication with at least three leads implanted into a patient's heart for delivering multi-chamber stimulation and shock therapy.

Referring to FIG. 4, a stimulation device 410 electrically couples to a patient's heart 412 using three leads 420, 424, and 430 to electrically communicate signals suitable for delivering multiple-chamber stimulation and shock therapy. The stimulation device 410 couples to an implantable right atrial lead 420 having at least an atrial tip electrode 422 to sense atrial cardiac signals and to supply right atrial chamber stimulation therapy. The atrial tip electrode 422 typically is implanted in the patient's right atrial appendage.

The stimulation device 410 is coupled to a "coronary sinus" lead 424 to sense left atrial and ventricular cardiac signals and to supply left chamber pacing therapy. The "coronary sinus" lead 424 is designed for placement in the "coronary sinus region" via the coronary sinus for positioning a distal electrode adjacent to the left ventricle and/or additional electrode(s) adjacent to the left atrium. The phrase "coronary sinus region" refers to the vasculature of the left ventricle including any portion of the coronary sinus, great cardiac vein, left marginal vein, left posterior ventricular vein, middle cardiac vein, and/or small cardiac vein or any other cardiac vein accessible by the coronary sinus.

The lead 424 may be used to supply stimulation pulses to a patient's left ventricle in biventricular pacing systems. Patients with chronic atrial fibrillation may be treated using biventricular VVIR pacemakers with left ventricular 424 and right ventricular 430 leads connected to the stimulation device 410. In patients with spontaneous sinus rhythm, biventricular DDDR stimulating devices may be implanted with an atrial lead 420 placed in the upper right atrium and two ventricular leads 424 and 430 connected to the left and right ventricles, respectively.

An illustrative coronary sinus lead 424 is configured to receive atrial and ventricular cardiac signals and to deliver left ventricular pacing therapy using at least a left ventricular tip electrode 426. The coronary sinus lead 424 delivers left atrial pacing therapy using at least a left atrial ring electrode 427. The coronary sinus lead 424 delivers shocking therapy using at least a left atrial coil electrode 428. U.S. patent application Ser. No. 09/457,277, filed Dec. 18, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), that are hereby incorporated herein by reference, contain a complete description of a suitable coronary sinus lead.

FIG. 4 shows the stimulation device 410 electrically coupled with the patient's heart 412 by an implantable right ventricular lead 430. The right ventricular lead 430 in the illustrative embodiment has a right ventricular tip electrode 432, a right ventricular ring electrode 434, a right ventricular (RV) coil electrode 436, and an SVC coil electrode 438. Typically, the right ventricular lead 430 is transvenously inserted into the heart 412 to place the right ventricular tip electrode 432 in the right ventricular apex, positioning the RV coil electrode 436 in the right ventricle and the SVC coil electrode 438 in the superior vena cava. Inserted in this manner, the right ventricular lead 430 is capable of receiving cardiac signals and delivering stimulation in the form of pacing and shock therapy to the right ventricle.

Figure 5:
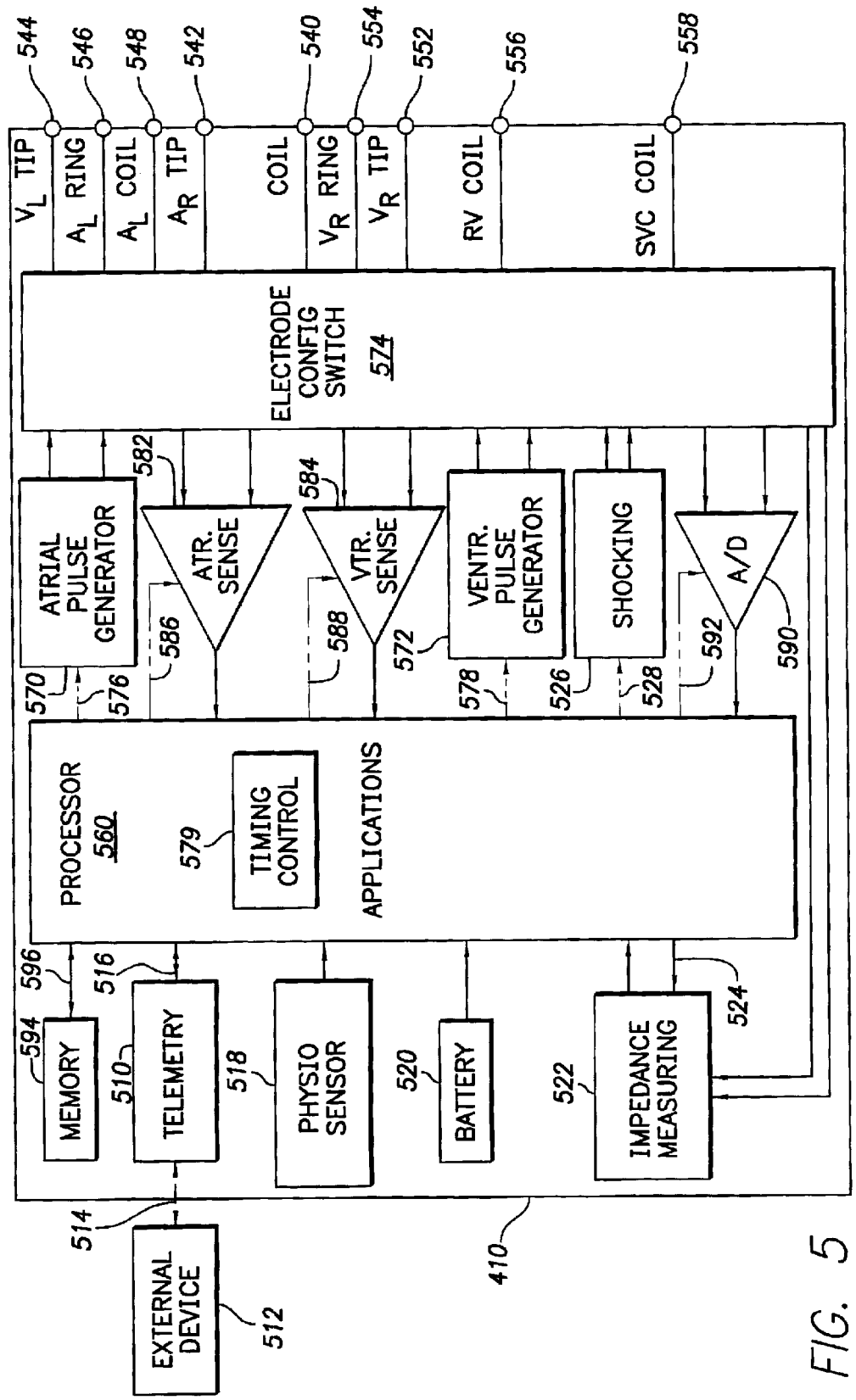
FIG. 5 is a functional block diagram that shows a multi-chamber implantable stimulation device illustrating basic elements of a stimulation device capable of cardioversion, defibrillation and pacing stimulation in four chambers of the heart.

Referring to FIG. 5, a simplified block diagram shows the multiple-chamber implantable stimulation device 410 that is capable of treating both fast and slow arrhythmias with stimulation therapy such as cardioversion, defibrillation, and pacing stimulation. The particular multi-chamber device is shown for illustration purposes only, and one of ordinary skill in the art can readily duplicate, eliminate, or disable various portions of circuitry in any desired combination to produce a device capable of delivering treatment in a desired chamber or chambers. Suitable treatments include, but are not limited to cardioversion, defibrillation and pacing stimulation, in either or both the atria and ventricles.

The housing 540 for the stimulation device 410, shown schematically in FIG. 5, is often referred to as the "can", "case" or "case electrode" and may be selected, for example by programming, to function as a return electrode for all "unipolar" modes. The housing 540 may also or otherwise be used as a return electrode alone or in combination with one or more of the coil electrodes, 428, 436 and 438, for delivering shocking stimulation to tissue. The housing 540 includes a connector (not shown) with a plurality of terminals 542, 544, 546, 548, 552, 554, 556, and 558. The terminals are shown schematically with, for convenience, names of the electrodes that are connected to the terminals shown next to the appropriate terminals. For example, at least a right atrial tip terminal ($A_R$ TIP) 542 is adapted for connection to the atrial tip electrode 422 to perform right atrial sensing and pacing.

To sense, pace, and shock in the left heart chambers, the connector includes at least a left ventricular tip terminal ($V_L$ TIP) 544, a left atrial ring terminal ($A_L$ RING) 546, and a left atrial shocking terminal ($A_L$ COIL) 548. The left ventricular tip terminal ($V_L$ TIP) 544 is adapted for connecting to the left ventricular ring electrode 425. The left atrial ring terminal ($A_L$ RING) 546 is configured to connect to the left atrial tip electrode 423. The left atrial shocking terminal ($A_L$ COIL) 548 is adapted to connect to the left atrial coil electrode 428.

The connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558 to support right chamber sensing, pacing and shocking. The right ventricular tip terminal ($V_R$ TIP) 552 is formed to connect to the right ventricular tip electrode 432. The right ventricular ring terminal ($V_R$ RING) 554 is adapted to connect to the right ventricular ring electrode 434. The right ventricular shocking terminal ($R_V$ COIL) 556 can connect to the RV coil electrode 435. The SVC shocking terminal (SVC COIL) 558 is configured to connect to the SVC coil electrode 438.

A programmable processor 560 is contained in the housing 540 and controls the various modes of stimulation therapy. The processor 560 can be implemented as any suitable control device such as a microcontroller, a controller, a microprocessor, a central processing unit, a signal processor, a digital signal processor, a state machine, a control logic, discrete control circuitry, or any similar control circuitry. In some embodiments, the processor 560 is designed specifically for controlling the delivery of stimulation therapy. The processor 560 may include RAM or ROM memory, logic and timing circuitry, state machine circuitry, and I/O circuitry. The processor 560 has a capability to process or monitor input signals or data, typically as a program code that is stored in a designated block of memory and executable by the processor 560. Details of design and operation of the processor 560 are well-known to those having ordinary skill in the art so that any suitable processor 560 may be used that can execute the functions described herein. Usage of microprocessor-based control circuits for performing timing and data analysis functions are well known by those having ordinary skill in the art.

Referring again to FIG. 5, an atrial pulse generator 570 and a ventricular pulse generator 572 generate pacing stimulation pulses that are delivered by the right atrial lead 420, the right ventricular lead 430, and/or the coronary sinus lead 424 via an electrode configuration switch 574. To therapeutically stimulate each of the four heart chambers, the atrial and ventricular pulse generators 570 and 572 may include dedicated, independent pulse generators, multiplexed pulse generators, or shared pulse generators. The processor 560 controls pulse generators 570 and 572 via appropriate respective control signals 576 and 578 to trigger or inhibit the stimulation pulses.

Processor 560 further includes timing control circuitry 579 to control timing of various stimulation pulse events such as pacing rate, atrio-ventricular (AV) delay, atrial interconduction (A-A) delay, or ventricular interconduction (V-V) delay, and others. The processor 560 and timing control circuitry 579 also track timing of refractory periods, blanking intervals, noise detection windows, evoked response windows, alert intervals, marker channel timing, and others. The timing control circuitry 579 times other various delays, event intervals, and timing windows that are well-known to those having ordinary skill in the art.

Switch 574 includes a plurality of switches for connecting the desired electrodes to the appropriate I/O circuits, allowing complete selective programming of electrode configuration. Typically, the processor 560 generates a control signal 580 that configures the switch 574 by selectively setting an appropriate combination of switches (not shown). In one example, the switches determine polarity of the simulation pulses from among possible unipolar, bipolar, combipolar polarities, and the like as are well-known to those having ordinary skill in the art.

Atrial sensing circuits 582 and ventricular sensing circuits 584 can detect cardiac activity in each of the four heart chambers by selective coupling to the right atrial lead 420, coronary sinus lead 424, and the right ventricular lead 430, through switch 574. The atrial (ATR. SENSE) 582 and ventricular (VTR. SENSE) 584 sensing circuits typically include amplifiers of various types such as dedicated sense amplifiers, multiplexed amplifiers, or shared amplifiers. The switch 574 determines sensing polarity of the cardiac signal by selectively configuring appropriate switches in a manner that is known to those having ordinary skill in the art. Stimulation and sensing polarity control is separate so that a clinician may program sensing polarity independently from programming of stimulation polarity.

The sensing circuits 582 and 584 each generally include one or more amplifiers, bandpass filtering, and a threshold detection circuit. Suitable amplifiers are precision amplifiers with programmable gain and/or automatic gain control functionality, a feature well-known to those having ordinary skill in the art. The sensing circuits 582 and 584 are programmed, either manually or automatically using a gain control algorithm to selectively sense a cardiac signal of interest. Automatic gain control enables the device 410 to effectively sense low amplitude cardiac signals, thereby managing the difficult problem of sensing low amplitude signal characteristics that occur in atrial or ventricular fibrillation conditions. Processor 560 receives output signals from atrial and ventricular sensing circuits 582 and 584. Processor 560 responds to the sensing signals by triggering or inhibiting atrial 570 and ventricular 572 pulse generators in the manner of "demand pacing" in response to the absence or presence of cardiac activity in the appropriate heart chambers.

The device 410 performs arrhythmia detection utilizing the atrial and ventricular sensing circuits 582 and 584 to sense cardiac signals. In arrhythmia detection, the device 410 determines whether a rhythm is physiologic or pathologic. As used herein, the term "sensing" refers to monitoring of a cardiac signal for determining the presence of a cardiac pulse. The term "detection" refers to processing of the sensed cardiac signals to determine the presence of an arrhythmia. Processor 560 classifies cardiac signals by comparing timing intervals between sensed events to a predefined rate zone limit and analyzing other characteristics to determine an appropriate remedial therapy. Measured and monitored timing intervals between sensed events include P-waves, R-waves, and depolarization signals associated with fibrillation which are sometimes referred to as "F-waves" or "Fib-waves", such as "atrial Fib-waves" and "ventricular Fib-waves". The timing intervals are compared to a predefined rate zone limit such as bradycardia, normal, low rate VT, high rate VT, fibrillation rate zones, and other rate limits that are known to those having ordinary skill in the art. Other analytical characteristics are selected from among, but not limited to sudden onset, stability, physiologic sensors, and morphology. The device 410 delivers remedial therapies such as bradycardia pacing, anti-tachycardia pacing, cardioversion shocks or defibrillation shocks, collectively referred to as "tiered therapy".

An analog-to-digital (A/D) data acquisition system 590 also receives cardiac signals for acquisition, conversion, and storage or communication. The data acquisition system 590 is configured to acquire intracardiac electrogram signals in analog format, convert the raw analog data into a digital signal, and store the digital signals for later processing and/or telemetric transmission to an external device 512. The data acquisition system 590 couples to the right atrial lead 420, the coronary sinus lead 424, and the right ventricular lead 430 through the switch 574 to acquire cardiac signal samples across any desired pair of electrodes.

The processor 560 is coupled to a memory 594 by a suitable data/address bus 596. Memory 594 stores programmable and/or automatically determined operating parameters used by the processor 560. Operating parameters are stored, determined, or modified, to customize the operation of the stimulation device 410 to needs of a particular patient. The operating parameters define, for example, pacing pulse amplitude, pulse duration, electrode polarity, stimulation rate, sensitivity, automatic features, arrhythmia detection criteria, and stimulation pulse characteristics. Stimulation pulse characteristics include amplitude, waveshape, and vector of each shocking pulse to be delivered to the patient's heart 412 within particular tiers of therapy. A feature of the device 410 is a capability to sense and store a relatively large amount of data, for example acquired from the data acquisition system 590. The data may then be used for subsequent analysis to guide device programming.

Operating parameters of the implantable device 410 may be non-invasively programmed into the memory 594 through a telemetry circuit 510 in telemetric communication with the external device 512, such as a programmer, transtelephonic transceiver, or a diagnostic system analyzer. The processor 560 sends a control signal 516 that activates the telemetry circuit 510. The telemetry circuit 510 communicates intracardiac electrograms and status information relating to the operation of the device 410 to the external device 512 through an established communication link 514.

In some embodiments, the stimulation device 410 can include a physiologic sensor 518, commonly called a "rate-responsive" sensor that is typically used to adjust pacing stimulation rate according to the exercise state of the patient. The physiological sensor 518 may also be used to detect changes in cardiac output, changes in the physiological condition of the heart, or diurnal changes in activity such as detecting sleep and wake states. The processor 560 responds by adjusting various pacing parameters such as rate, AV Delay, V-V Delay, and the like, at which atrial and ventricular pulse generators 570 and 572 generate stimulation pulses.

Although the example shows the physiological sensor 518 included within the stimulation device 410, the physiologic sensor 518 may otherwise be located external to the stimulation device 410. An external physiological sensor 518 may be implanted within a patient or carried by the patient. A common type of rate responsive sensor is an activity sensor such as an accelerometer or a piezoelectric crystal, mounted within the housing 540 of the stimulation device 410 that generates a measurable electrical potential when a mechanical stress resulting from physical activity is applied to the sensor. By analyzing the signal from a piezoelectric activity sensor, a rate-responsive pacemaker can detect various conditions or determine how frequently pacing pulses should be applied to the patient's heart.

Multiple other types of physiologic sensors are suitable, including for example sensors that measure central venous blood temperature, blood oxygen content, blood pH level, QT time interval, respiration rate and/or minute ventilation, ventricular gradient, and other parameters. Generally any sensor capable of sensing a physiological parameter that corresponds to the exercise state of the patient may be used although aspects of response time, unpredictable emotionally-induced variations, side effects, and performance variability among different patients are important considerations in selection.

Some embodiments may include a "sleep state" or diurnal sensor that can detect sleep and wake states. One diurnal sensor is called an "activity variance" sensor in which an activity sensor is monitored diurnally to detect the low variance in the measurement that corresponds to the sleep state. U.S. Pat. No. 5,476,483 (Bornzin et al.) describes a complete description of the activity variance sensor.

The stimulation device 410 includes a battery 520 that supplies operating power to all of the circuits shown in the device 410. For a stimulation device 410 that is capable of delivering a shocking therapy, a suitable battery 520 is capable of operating at low current drains for long periods of time, but also be capable of generating high-current pulses for capacitor charging when the patient requires a shock pulse. A suitable battery 520 has a predictable discharge characteristic so that elective replacement time can be detected. Most typically, the device 410 employs lithium/silver vanadium oxide batteries for most, if not all, current devices.

The device 410 also has an impedance measuring circuit 522 which is enabled by a control signal 524 from the processor 560. The impedance measuring circuit 522 is useful for one or more of several functions. The impedance measuring circuit 522 performs lead impedance surveillance during the acute and chronic phases for proper lead positioning and detection of lead dislodgment. The impedance measuring circuit 522 permits detection of electrode operability and automatic switching from an inoperable pair to an operable pair if dislodgment occurs. Impedance measuring circuit 522 is useful for measuring respiration or minute ventilation that can be applied to rate responsive pacing or other automatic control operations. The impedance measuring circuit 522 can be configured to measure thoracic impedance to determine shock thresholds. Impedance measurements can be used to detect implant time of the device 410. The impedance measuring circuit 522 can be used for many other various operations including measurements of stroke volume, detection of heart value opening, and the like. The impedance measuring circuit 522 can be coupled to the switch 574 so that any desired electrode may be used.

In some embodiments, the stimulation device 410 is configured to operate as an implantable cardioverter/defibrillator (ICD) device. An ICD device detects arrhythmia conditions and responds to the detected arrhythmia condition by automatically applying a suitable electrical shock therapy to the heart for the purpose of terminating the detected arrhythmia. The processor 560 controls a shocking circuit 526 by way of a control signal 528. The shocking circuit 526 generates shocking pulses of low (up to 0.5 Joules), moderate (0.5–10 Joules), or high energy (11 to 40 Joules), under control by the processor 560. Shocking pulses are applied to the patient's heart 412 through at least two shocking electrodes, selected from the left atrial coil electrode 428, the RV coil electrode 436, and/or the SVC coil electrode 438. The housing 540 may be used as an active electrode in combination with the RV coil electrode 436, or as part of a split electrical vector using the SVC coil electrode 438 or the left atrial coil electrode 428, for example using the RV electrode as a common electrode.

Cardioversion shock energy is a relatively low to moderate energy level to reduce pain felt by the patient. The cardioversion shock can be synchronized with an R-wave cardiac signal and can be part of tachycardia treatment. Defibrillation shock energy is generally a moderate to high energy level, for example corresponding to thresholds in the range of 5–40 Joules, and is delivered asynchronous with respect to intrinsic cardiac activity since R-waves may be insufficiently organized for synchronous stimulation utility. Defibrillation shocks are applied exclusively to treatment of fibrillation. Processor 560 is capable of controlling the synchronous or asynchronous delivery of the shocking pulses.

An illustrative technique for preventing and treating sleep apnea includes control actions based on overdrive pacing, for example atrial overdrive pacing. A stimulation device 410 overdrive paces at a rate faster than the patient's underlying rate, generating an atrial stimulation pulse to the atrium at a time in the cardiac cycle just prior to the occurrence of a spontaneous atrial depolarization.

One of several rate-determination techniques may be used to find a suitable overdrive rate including: (1) an automatic diurnal rate determination method, (2) a method using an automatic stepped increase over a calculated average atrial rate, (3) a technique based on negative hysteresis, and (4) other techniques. The goal of a suitable overdrive pacing method is to stimulate the atrium at a time in the pacing cycle immediately prior to a natural depolarization. Overdrive pacing stimulates the heart at a rate just slightly faster than what the heart's predicted natural rate.

The automatic diurnal rate determination method tracks diurnal rate which varies throughout the day, and may be automatically determined, for example using the method described in Bornzin et al., "Adjusting Heart Rate During Sleep Using Activity Variance," PACE, Vol. 17, (Pt. II) pp. 1933–1938 (November 1994) and in U.S. Pat. No. 5,476,483 (Bornzin et al.), which documents are incorporated herein by reference.

A typical patient's heart rate and other physiological processes and parameters, for example blood pressure, temperature, endogenous corticosteroids, and others, demonstrate a rhythmic variation during the day. The variation is a circadian or "diurnal" variation and may be termed a diurnal rate. A typical diurnal variation shows a heart rate that peaks during the day when the patient is awake and active, and drops to a lowest rate or resting rate during early morning hour sleep.

The automatic diurnal rate determination method operates by determining the diurnal rate of a particular patient and setting "base rate" of the patient's pacemaker to a value that is a predetermined value less than the determined diurnal rate when the patient is sleeping. Base stimulation rate is the minimum heart rate for the patient, below which the natural heart rate may not fall without having the pacemaker deliver a pacing pulse.

The stimulation device 410 modulates base rate as a function of diurnal rate to track or follow diurnal rate when the patient is asleep or inactive. Device base rate need not be a fixed rate, but may have a range of values at times when the patient is asleep or inactive. The automatic diurnal rate determination method includes actions of determining patient-specific diurnal variation and deriving a suitable diurnal base rate for the patient as a function of the time of day that, for most cardiac cycles, assures overdrive pacing.

Figure 6:
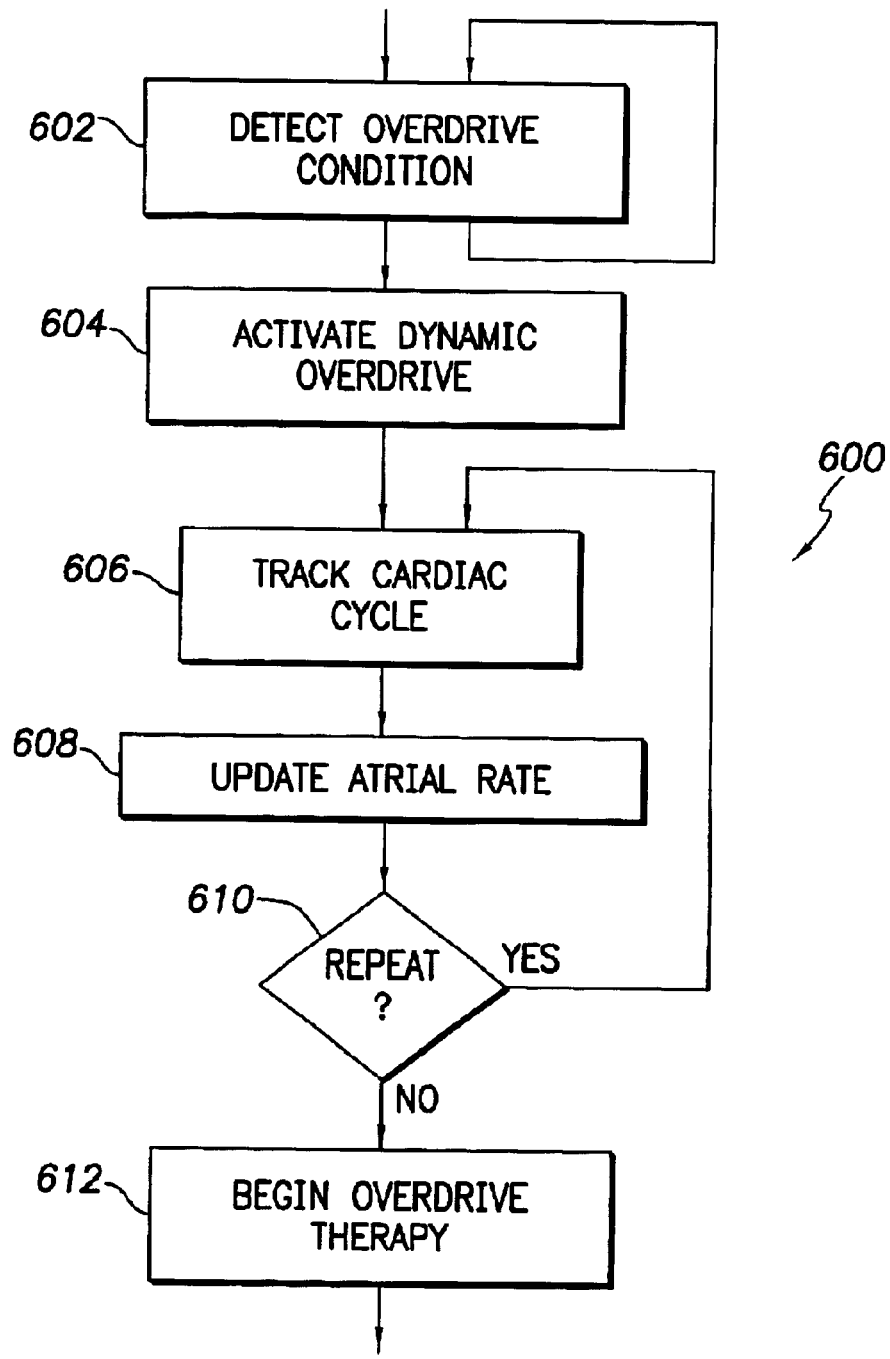
FIG. 6 is a flowchart depicts a first example of a method for overdrive pacing.

Referring to FIG. 6, a flowchart depicts a first example of a method for overdrive pacing. Overdrive pacing is defined as the generation and delivery of cardiac pacing pulses at a rate higher than the underlying intrinsic cardiac rate. One technique for overdrive pacing is dynamic overdrive pacing which involves tracking of atrial intrinsic activity, typically called P-waves, and generating pacing pulses in the atrium at a rate that exceeds the intrinsic atrial rate. Accordingly when a P-wave is detected, the stimulation device 410 increases the pacing rate by a small amount to induce pacing but not so greatly that the heart rate is substantially elevated. In a detect overdrive condition action 602, the system detects a patient condition that would be assisted by overdrive pacing.

In one example, the stimulation device 410 activates dynamic overdrive pacing upon detection of a sleep condition to prevent a sleep apnea condition. In another example, the stimulation device 410 activates dynamic overdrive pacing upon detection of a sleep apnea condition to treat the condition. Following detection of the overdrive condition, the stimulation device 410 activates dynamic overdrive pacing 604 including setting of an assured overdrive rate. The assured overdrive rate may be a preselected rate, for example a rate set by a health care provider via programmer communication, that is known to be sufficiently higher than a possible intrinsic rate. The assured overdrive rate may alternatively be set by monitoring the cardiac rate, for example the paced rate, cardiac rate under inhibited pacing, or the rate of intrinsic heart depolarization alone, and adding a suitable increment. In a particular example, the underlying sinus rate may be 70 bpm and the assured overdrive rate set to 80 bpm.

Over multiple cardiac cycles, the stimulation device 410 tracks atrial pacing and any intrinsic atrial depolarization in a track cardiac cycle action 606 and uniformly decrements the atrial pacing rate in an update atrial rate action 608, both actions being repeated in a loop 610. The track cardiac cycle action 606 senses atrial signals and delivers an atrial pacing pulse unless inhibited by an intrinsic atrial depolarization. Generally, the track cardiac cycle action 606 monitors whether the cardiac cycles are paced or inhibited and permits the pacing rate to be reduced for cycles that are not inhibited. Once a cycle is inhibited, the pacing rate is held constant at a base overdrive rate and the number of cycles is counted between inhibited cycles. In one example, the base overdrive rate is set to the pacing rate at which the inhibited cycle occurs. In another example, the base overdrive rate is set to the pacing rate of the inhibited cycle plus a preselected decrement at which the rate is reduced when scanning for the base overdrive rate. In a third example, the base overdrive rate is set to the pacing rate of the inhibited cycle plus half the preselected decrement value. If the number of cycles between inhibited cycles is greater than a selected number, for example sixteen, then the rate is reset to the assured overdrive rate to begin a new search for the baseline overdrive rate.

Until the inhibited cycle, the update atrial rate action 608 reduces the pacing rate by the preselected decrement such as a rate decrement, for example 2 bpm, or a interval length increment, for example 15 msec. The pacing rate may be decreased for each cardiac cycle or may be decreased in steps with the individual steps lasting for a selected number of cardiac cycles. The update atrial rate action 608 resets the pacing rate to the assured overdrive rate if warranted by too frequent inhibited cycles. The pacing rate can be further reduced, for example in response to the patient entering a resting or sleep state, by occasionally testing for intrinsic cardiac pacing at a lower rate. In one example, the rate can be further reduced by the preselected decrement value at preselected time intervals or a preselected number of cardiac cycles. Alternatively, the rate can be reset to the assured overdrive rate at the preselected time intervals or preselected number of cardiac cycles to restart the search for the base overdrive rate.

The scanning technique for determining a base overdrive rate is useful to obtain a high percentage of cardiac cycles that are paced and a low percentage of inhibited cycles. The baseline overdrive rate may be termed a dynamic overdrive conversion rate.

In alternative embodiments, dynamic overdrive pacing can be controlled by modifying parameters other than the base pacing rate. In one example, the ventricle-to-ventricle (V-V) interval may be reduced to increase the pacing rate to an overdrive level. In another example, atrial-to-ventricular (A-V) interval may be reduced to overdrive the intrinsic pacemaking of the heart.

The stimulation device 410 upon determining the dynamic overdrive conversion rate can begin an overdrive therapy action 612. In one example, the stimulation device 410 can detect a sleeping condition of the patient and initiate a sleep apnea prevention overdrive rate therapy action 612. Sleep apnea commonly occurs when the heart rate manifests a bradycardia condition. The stimulation device 410 prevents sleep apnea by generating pacing pulses at a rate higher than the sinus rate during sleep. In one example, the apnea prevention rate is set to a rate a preselected programmable rate increment, such as five bpm, over the sinus rate at sleep. Accordingly, the stimulation device 410 paces at a rate higher than the sinus rate when the patient is sleeping and, when the patient is awake, either pacing at a programmed rate or a rate that tracks p-waves by dynamic overdrive pacing.

Figure 7:
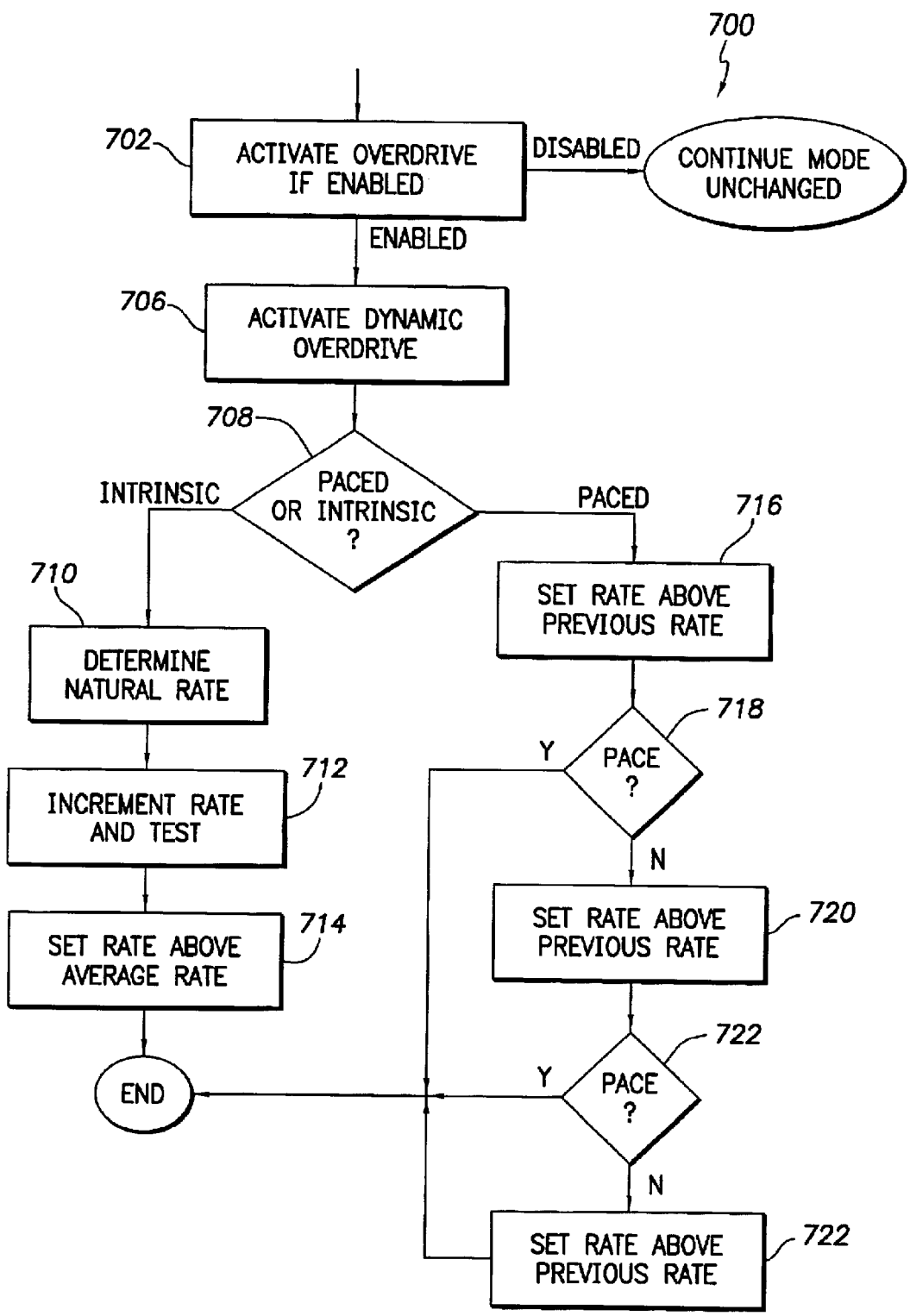
FIG. 7 is a flowchart that depicts actions that take place in an example of dynamic overdrive (DAO) pacing.
Figure 8:
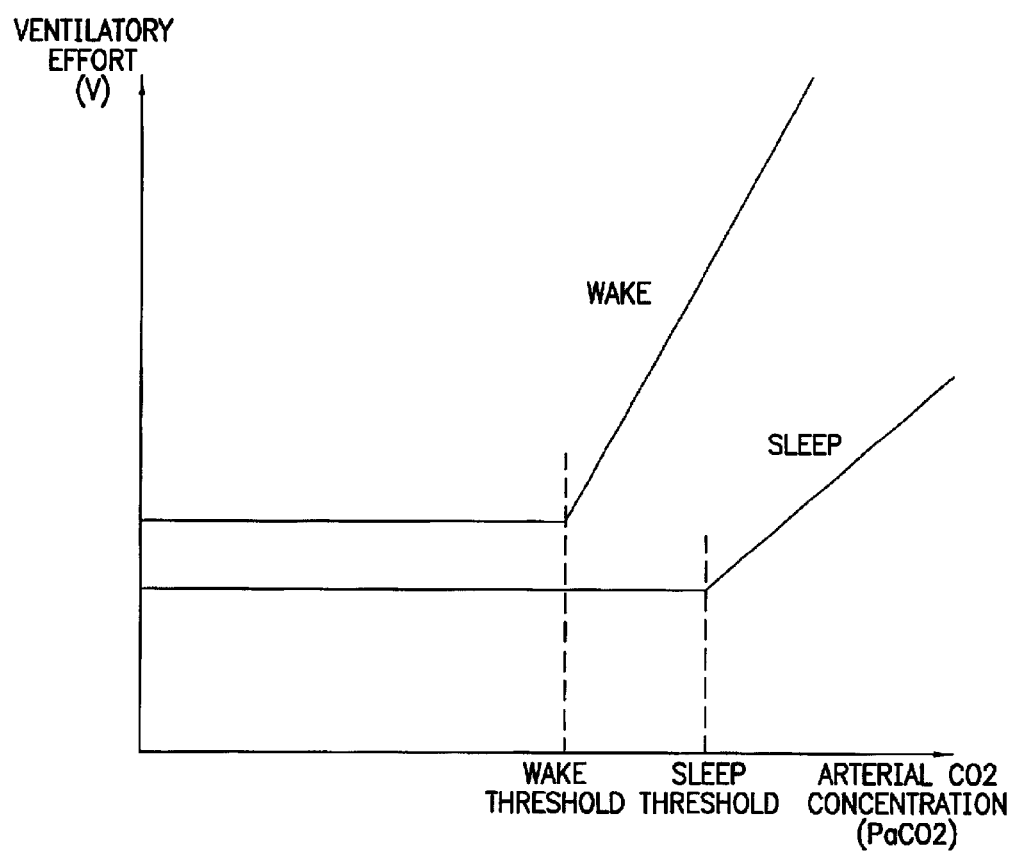
FIG. 8 is a graph that illustrates the mechanism of sleep apnea by correlating ventilatory effort to arterial partial pressure of carbon dioxide ($PaCO_2$).

Referring to FIG. 7, a flowchart depicts an example of a method of overdrive pacing based on applying a step increase to a measured atrial rate. The automatic diurnal rate determination method involves iteratively calculating the diurnal base rate as a function of a running average of the sensed heart rate. If a sensed intrinsic heart rate signal is not available, for example in the case of a diseased or defective heart that must be paced, the technique involves predicting a running average of an activity signal representative of a natural heart rate signal. In a more specific example, an average heart rate signal and/or activity signal may be digitally filtered using both a relatively short time constant and a relatively long time constant. An example of suitable time constants is approximately 1.6 and 38 minutes, respectively.

The long time constant resists short-term fluctuations in the heart rate or activity signals, giving a stable average pacing rate that gradually transitions over time. The short time constant produces filtered heart rate signal or activity signal components that are more responsive to short-term variations, allowing average heart rate signal components indicative of more rapid heart rate fluctuations.

The method using an automatic stepped increase over a calculated average atrial rate sets and controls overdrive pacing rate based on step increments that may introduce controlled variability into the cardiac rate. In a dual-chamber pacemaker, atrial rate may be monitored beat-for-beat or as an average of a number of beats. Control based on averaged atrial rate prevents premature atrial contractions (PACs) from falsely changing pacing rate.

In an activate action 702, a predefined programming command may selectively invoke automatic overdrive random pacing. If not enabled, the stimulation device 702 continues to operate in a previously-selected operating mode 704 in conventional manner. If automatic overdrive random rate pacing is enabled, appropriate programming commands 706 initiate the overdrive pacing. Commands may include selection of the number m[P] of consecutive P-to-P intervals that are measured to determine an average atrial rate, delta step size of pacing rate is increase, number n[P] of consecutive cycles of pacing rate increase by the delta step size, and others.

Once activated with operating parameters, stimulation device 410 executes a test action 708 to determine whether atrial pacing or intrinsic P-wave sensing and tracking occurs. If P-waves are sensed and P-wave tracking is occurring, in a determine natural rate action 710, stimulation device 410 measures the native or natural atrial rate based on, for example, the average P-to-P interval over m[P] consecutive cycles. Parameter m[P] may be a programmable integer typically in a range from 2–32 cycles.

In an increment rate action 712, the stimulation device 410 is autoprogrammed to a base rate that is a step increment of predetermined size faster than the measured atrial rate. Once the stimulation device 410 determines the average atrial rate, the stimulation rate is set for one cycle to a value that is faster than the measured average atrial rate by the programmed delta step size 714. A suitable range of delta step size is typically a range from 2–10 bpm. If atrial stimulation is already occurring when the P-wave tracking/atrial pacing test is performed, then the stimulation rate is set for one cycle to a value that is faster than the atrial pacing rate by the amount delta step size amount 716. During the single step increased rate cycle, stimulation device 410 makes another determination regarding whether atrial pacing occurs 718.

If stimulation device 410 does not sense an intrinsic P-wave and generates an atrial stimulation pulse at the end of the appropriate escape interval, the pacing rate is again increased by a second delta step size amount 720. The updated pacing rate is twice the delta step size from the initial atrial pacing rate or the measured average intrinsic atrial rate.

During the twice delta step size increment cycle, stimulation device 410 again determines whether atrial pacing occurs 722. If the device delivers an atrial stimulation pulse upon failure to sense an intrinsic P-wave, then pacing rate is again increased for one cycle by a third delta step size amount 724, a three times delta step increase over the initial rate. After the three times delta incremented pacing cycle or whenever atrial pacing fails to occur, pacing rate returns to either the newly autoprogrammed base rate, a sensor-indicated rate (SIR) for a system utilizing the physiological sensor 518, or a minimum pre-programmed base rate, whichever is greater.

In a loop that includes a step increment and test actions 712 to 724, the pacing interval is adjusted by the predetermined step increment above the autoprogrammed base rate on a cycle-by-cycle basis for a preset number of cycles. After the predetermined number of cycles, stimulation device 410 stimulates the heart at the autoprogrammed base rate. The incrementing loop assures that atrial overdrive pacing controls rate to automatically increase for the cycles in the loop by a predetermined delta rate.

The method attains atrial overdrive pacing at single-cycle rates that vary in prescribed step increments over an automatically-programmed base rate to assure atrial pacing. If the intrinsic average atrial rate increases to a rate faster than the autoprogrammed base rate to a newly determined average atrial rate, then stimulation device 410 automatically reprograms the base rate to the new intrinsic average rate plus the step size. After the stepped increases, pacing rate returns to the newly autoprogrammed base rate, a sensor-indicated rate (SIR) for a system utilizing the physiological sensor 518, or a minimum pre-programmed base rate, whichever be used. Because the rate of overdrive pacing changes by the delta amount on a cycle-by-cycle basis, the technique may be termed "automatic overdrive random rate pacing".

The possible pacing rates may alternate or sequence in a prescribed pattern. For example, rate may return to the highest possible rate for the first k loops, the next highest rate for the next I loops, and finally to the lowest rate after the (I+k)th loop, where k and I are programmable integers selected from a range of 0 to 8.

Other return patterns, whether set by programming or default, may otherwise be used. For example, a default return pattern may be an obligatory return to the sensor-indicated rate if rate-responsive pacing is active, otherwise returning to the most recently-determined average rate plus the delta increase, except every m[P] loop returning to the base rate.

For any return method, a new average rate may be determined at regular intervals, for example every few minutes, so that the average rate both increases and decreases to determine the patient's intrinsic rhythm. As a result of the technique, overdrive pacing occurs most cardiac cycles with the overdrive rate varying on a cycle-by-cycle basis. The average overdrive rate is a rate that generally tracks changes in the patient's intrinsic rhythm.

The delta step size may relate to a fixed rate increment or a fixed escape interval decrement, or may be variable, for example may vary from one cycle to the next in the incrementing loop.

The technique based on hysteresis applies negative hysteresis every cycle.

While the invention has been described with reference to various embodiments, it will be understood that these embodiments are illustrative and that the scope of the invention is not limited to them. Many variations, modifications, additions and improvements of the embodiments described are possible. For example, those of ordinary skill in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. An implantable cardiac stimulation device comprising:
   a first sensor that is capable of sensing intrinsic cardiac activity and generating corresponding signals;
   circuitry that is connected to the sensor to receive signals from the sensor, wherein the circuitry is operative to process the signals to determine an intrinsic heart rate;
   a second sensor that is capable of sensing a physiologic parameter;
   circuitry that is connected to the second sensor and that is operative to determine a potential sleep apnea condition based on the sensed physiologic parameter;
   one or more pulse generators that are capable of generating cardiac pacing pulses to be delivered to the patient; and
   a control circuit that is responsive to detection of the potential sleep apnea condition to control the one or more pulse generators to pace at an overdrive pacing rate based on the intrinsic heart rate to prevent sleep apnea.

2. An implantable cardiac stimulation device according to claim 1 wherein the control circuit comprises an executable control logic that includes a logic capable of detecting a sleep condition, and a logic capable of controlling the one or more pulse generators with a timing based on the sensed intrinsic heart rate to overdrive the intrinsic heart rate to prevent sleep apnea.

3. An implantable cardiac stimulation device according to claim 1 wherein the control circuit comprises an executable control logic including a logic for detecting a sleep condition based on the physiological parameter, and a logic capable of controlling the one or more pulse generators with a timing based on the sensed intrinsic heart rate to overdrive the intrinsic cardiac electrical phenomena to prevent sleep apnea.

4. An implantable cardiac stimulation device according to claim 1 further comprising:
a sensor implantable into a chamber of the heart that is capable of sensing intrinsic electrical phenomena; and
a pulse generator of the one or more pulse generators that is capable of generating pacing pulses based on timing of the sensed intrinsic electrical phenomena to dynamically overdrive the intrinsic electrical phenomena, the generated cardiac pacing pulses being capable of preventing sleep apnea.

5. An implantable cardiac stimulation device according to claim 1 wherein the control circuit comprises an executable control logic that is capable of distinguishing between a rest or sleeping condition and a waking condition of a patient based on the physiological parameter, confirming a sleep apnea condition based on the physiological parameter, and generating pacing pulses based on timing of the sensed intrinsic heart rate to dynamically overdrive the intrinsic cardiac electrical phenomena, the generated cardiac pacing pulses being capable of preventing sleep apnea.

6. An implantable cardiac stimulation device according to claim 1 further comprising:
an impedance sensor that is capable of sensing one or more respiration parameters; and
wherein the control circuit is coupled to the one or more pulse generators and to the impedance sensor, the control circuit comprising an executable control logic that is capable of distinguishing between a sleeping condition and a waking condition of a patient based on the one or more respiration parameters, and generating pacing pulses based on timing of the sensed intrinsic heart rate to dynamically overdrive the intrinsic cardiac electrical phenomena, the generated cardiac pacing pulses being capable of preventing sleep apnea.

7. An implantable cardiac stimulation device comprising:
a sensor that is capable of sensing intrinsic cardiac electrical phenomena;
a heart rate determination device that is connected to the sensor and is operative to determine an intrinsic heart rate based on the sensed intrinsic cardiac electrical phenomena;
circuitry that is capable of generating cardiac pacing pulses at an overdrive pacing rate based on the intrinsic heart rate; and
a sleep apnea determination device that is operative to determine when a potential sleep apnea condition exists, and that is responsive to the potential sleep apnea condition to control the circuitry to generate pacing pulses at the overdrive pacing rate to prevent apnea.

8. An implantable cardiac stimulation device according to claim 7 wherein the sleep apnea determination device comprises a controller that comprises an executable control logic that includes a logic capable of detecting a sleep condition, and a logic capable of controlling one or more pulse generators with a timing based on the sensed intrinsic cardiac electrical phenomena to overdrive the intrinsic cardiac electrical phenomena.

9. An implantable cardiac stimulation device according to claim 7 further comprising:
a physiological sensor that is capable of sensing a physiological parameter; and
wherein the sleep apnea determination device comprises a controller coupled to the sensor, the controller comprising an executable control logic that detects a sleep apnea condition based on the sensed physiological parameter and controls one or more pulse generators with an overdrive pacing rate based on the sensed intrinsic cardiac electrical phenomena.

10. A method of operating an implantable cardiac stimulation device comprising:
monitoring cardiac activity;
determining an intrinsic heart rate based on the monitored activity;
monitoring a physiologic parameter for a potential sleep apnea condition; and
generating overdrive pacing pulses at an overdrive pacing rate in response to determining a potential sleep apnea condition, wherein the overdrive pacing rate is based on the intrinsic heart rate to prevent sleep apnea.

11. A method according to claim 10 further comprising:
detecting a sleep condition; and
generating the dynamic overdrive pacing pulses upon detecting the sleep apnea condition.

12. A method according to claim 10 further comprising:
sensing a physiological parameter;
distinguishing between a sleeping condition and a waking condition of a patient based on the sensed physiological parameter;
generating cardiac pacing pulses based on timing of the sensed intrinsic cardiac electrical phenomena; and
dynamically overdriving the heart.

13. An implantable cardiac stimulation device comprising:
means for determining an intrinsic heart rate;
means for detecting a potential sleep apnea condition; and
means for overdrive pacing the heart at a rate based on the intrinsic heart rate in response to detection of a potential sleep apnea condition to prevent sleep apnea.

14. An implantable cardiac stimulation device according to claim 13 wherein the means for detecting a potential sleep apnea condition comprises means for detecting a sleep condition.

15. An implantable cardiac stimulation device comprising:
a first sensor that is capable of sensing intrinsic cardiac activity and generating corresponding signals;
circuitry that is connected to the sensor to receive signals from the sensor, wherein the circuitry is operative to process the signals to determine an intrinsic heart rate;
a second sensor that is capable of sensing a physiologic parameter;
circuitry that is connected to the second sensor and that is operative to determine a potential sleep apnea condition based on the sensed physiologic parameter;
one or more pulse generators that are capable of generating cardiac pacing pulses to be delivered to the patient; and
a control circuit that is responsive to detection of the potential sleep apnea condition to control the one or more pulse generators to dynamically overdrive the intrinsic heart rate.

16. An implantable cardiac stimulation device according to claim 15 wherein the control circuit comprises an executable control logic that detects a sleep apnea condition and controls the one or more pulse generators with a timing based on the sensed intrinsic heart rate and is capable of terminating the detected sleep apnea condition.

17. An implantable cardiac stimulation device according to claim 15 wherein the control circuit comprises an executable control logic that detects a sleep apnea condition based on the sensed physiological parameter and controls the one or more pulse generators with a timing based on the sensed intrinsic heart rate that is capable of terminating the detected sleep apnea condition.

18. An implantable cardiac stimulation device according to claim 17 wherein the second sensor detects Cheyne-Stokes respiration.

19. An implantable cardiac stimulation device according to claim 15 further comprising:
an impedance sensor that is capable of sensing one or more respiration parameters; and
wherein the control circuit is coupled to the one or more pulse generators and to the impedance sensor, the control circuit comprising an executable control logic that is capable of distinguishing between a sleeping condition and a waking condition of a patient based on the one or more respiration parameters, and generating pacing pulses based on timing of the sensed intrinsic heart rate to dynamically overdrive the intrinsic cardiac electrical phenomena, the generated cardiac pacing pulses being capable of preventing sleep apnea.

20. An implantable cardiac stimulation device according to claim 19 further comprising:
an oxygen sensor that is capable of measuring blood oxygen concentration; and
wherein the control circuit is coupled to the one or more pulse generators and to the impedance sensor, the control circuit comprising an executable control logic that is capable of detecting a sleep apnea condition of a patient based on a blood oxygen concentration indicative that blood oxygen level is depressed during sleep, and generating pacing pulses based on timing of the sensed intrinsic heart rate to dynamically overdrive the intrinsic heart rate, the generated cardiac pacing pulses being capable of terminating sleep apnea.

21. An implantable cardiac stimulation device according to claim 15 further comprising:
a carbon dioxide sensor that is capable of measuring blood carbon dioxide concentration; and
wherein the control circuit is coupled to the one or more pulse generators and to the impedance sensor, the control circuit comprising an executable control logic that is capable of detecting a sleep apnea condition of a patient based on a blood carbon dioxide concentration indicative that blood oxygen level is depressed during sleep, and generating pacing pulses based on timing of the sensed intrinsic heart rate to dynamically overdrive the intrinsic cardiac electrical phenomena, the generated cardiac pacing pulses being capable of terminating sleep apnea.

22. An implantable cardiac stimulation device comprising:
a sensor that is capable of sensing intrinsic cardiac electrical phenomena;
a heart rate determination device that is connected to the sensor and is operative to determine an intrinsic heart rate based on the sensed intrinsic cardiac electrical phenomena;
circuitry that is capable of generating cardiac pacing pulses at a dynamic overdrive pacing rate based on the intrinsic heart rate; and
a sleep apnea determination device that is operative to determine when a potential sleep apnea condition exists, and that is responsive to the potential sleep apnea condition to control the circuitry to generate pacing pulses at the dynamic overdrive pacing rate.

23. An implantable cardiac stimulation device according to claim 22 further comprising:
a physiological sensor that is capable of detecting an abnormal breathing pattern; and
wherein the sleep apnea determination device comprises a controller coupled to the physiologic sensor, the controller comprising an executable control logic that detects the abnormal breathing pattern and controls one or more pulse generators with a timing based on the sensed intrinsic cardiac electrical phenomena.

24. An implantable cardiac stimulation device according to claim 23 wherein the abnormal breathing pattern is indicative of Cheyne-Stokes respiration.

25. An implantable cardiac stimulation device according to claim 22 further comprising:
an impedance sensor that is capable of sensing one or more respiration parameters; and
wherein the sleep apnea determination device comprises a controller coupled to the impedance sensor, the controller comprising an executable control logic that is capable of detecting a sleep apnea condition of a patient based on the one or more respiration parameters, and generating pacing pulses based on timing of the sensed intrinsic cardiac electrical phenomena to generate dynamic overdrive pacing pulses.

26. An implantable cardiac stimulation device according to claim 22 further comprising:
an oxygen sensor that is capable of measuring blood oxygen concentration; and
wherein the sleep apnea determination device comprises a controller coupled to the impedance sensor, the controller comprising an executable control logic that is capable of detecting a sleep apnea condition of a patient based on a blood oxygen concentration indicative that blood oxygen level is depressed during sleep, and generating pacing pulses based on timing of the sensed intrinsic cardiac electrical phenomena to dynamically overdrive the intrinsic cardiac electrical phenomena, the generated cardiac pacing pulses being capable of terminating sleep apnea.

27. A method of operating an implantable cardiac stimulation device comprising:
monitoring cardiac activity;
determining an intrinsic heart rate based on the monitored activity;
monitoring a physiologic parameter for a potential sleep apnea condition; and
generating dynamic overdrive pacing pulses eta dynamic overdrive pacing rate in response to determining a potential sleep apnea condition, wherein the dynamic overdrive pacing rate is based on the intrinsic heart rate.

28. A method according to claim 27 further comprising:
detecting a sleep apnea condition; and
generating the dynamic overdrive pacing pulses upon detecting the sleep apnea condition.

29. A method according to claim 27 further comprising:
detecting Cheyne-Stokes respiration; and
generating the overdrive pacing pulses upon detecting the Cheyne-Stokes respiration.

* * * * *